US00PP14096P29

(12) United States Plant Patent
Hoogendoorn

(10) Patent No.: US PP14,096 P2
(45) Date of Patent: Aug. 26, 2003

(54) ALSTROEMERIA PLANT NAMED 'STAMARIA'

(75) Inventor: Cornelis Arie Hoogendoorn, Nieuwkoop (NL)

(73) Assignee: Van Zanten Plants B.V., Hillegom (NL)

( * ) Notice: Subject to any disclaimer, the term of this patent is extended or adjusted under 35 U.S.C. 154(b) by 0 days.

(21) Appl. No.: 10/200,301

(22) Filed: Jul. 22, 2002

(51) Int. Cl.[7] ..... A01H 5/00
(52) U.S. Cl. ..... Plt./309
(58) Field of Search ..... Plt./309

(56) References Cited

U.S. PATENT DOCUMENTS

PP11,662 P * 11/2000 van Andel ..... Plt./309

OTHER PUBLICATIONS

UPOV ROM GTITM Computer Database, GTI JOUVE Retrieval Software Jun. 2002/06, citation(s) for 'Stamaria'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Alstroemeria plant named 'Stamaria', characterized by its erect flowering stems; light orange and dark pink bi-colored flowers with dark purple spots and stripes; and excellent postproduction longevity.

1 Drawing Sheet

BOTANICAL CLASSIFICATION/CULTIVAR DESIGNATION

*Alstroemeria hybrida* cultivar Stamaria.

BACKGROUND OF THE INVENTION

The present Invention relates to a new and distinct cultivar of Alstroemeria plant, botanically known as *Alstroemeria hybrida,* commercially used as a cut flower Alstroemeria, and hereinafter referred to by the name 'Stamaria'.

The new Alstroemeria is a product of a planned breeding program conducted by the Inventor in Aalsmeer, The Netherlands. The objective of the breeding program was to develop new cut flower Alstroemeria cultivars with strong plant growth, attractive flower colors and excellent postproduction longevity.

The new Alstroemeria originated from a cross made by the Inventor in June, 1995 in Aalsmeer, The Netherlands, of a proprietary *Alstroemeria hybrida* selection identified as 89T935- 1, not patented, as the female, or seed, parent with a proprietary *Alstroemeria hybrida* selection identified as 86G713-1, not patented, as the male, or pollen, parent. The new Alstroemeria was discovered and selected by the Inventor as a single flowering plant within the progeny of the stated cross in a controlled environment in Aalsmeer, The Netherlands in June, 1996. The selection of this new Alstroemeria was based on its attractive flower coloration.

Asexual reproduction of the new cultivar by root divisions taken in a controlled environment in Aalsmeer, The Netherlands, since June, 1996, has shown that the unique features of this new Alstroemeria are stable and reproduced true to type in successive generations of asexual propagation.

SUMMARY OF THE INVENTION

Plants of the cultivar Stamaria have not been observed under all possible environmental conditions. The phenotype may vary somewhat with variations in environment such as temperature and light intensity without, however, any variance in genotype.

The following traits have been repeatedly observed and are determined to be the unique characteristics of 'Stamaria'. These characteristics in combination distinguish 'Stamaria' as a new and distinct cultivar:

1. Erect flowering stems.
2. Light orange and dark pink bi-colored flowers with dark purple-colored spots and stripes.
3. Excellent postproduction longevity.

Plants of the new Alstroemeria are most similar to plants of the parent selections. However, plants of the new Alstroemeria differ from plants of the parents in flower coloration as plants of the female parent have red-colored flowers and plants of the male parent have yellow-colored flowers.

Plants of the new Alstroemeria can be compared to plants of the cultivar Staloren, disclosed in U.S. Plant Pat. No. 11,662. In side-by-side comparisons conducted in Rijsenhout, The Netherlands, plants of the new Alstroemeria differed primarily from plants of the cultivar Staloren in flower coloration as plants of the cultivar Staloren had salmon orange-colored flowers.

BRIEF DESCRIPTION OF THE PHOTOGRAPH

The accompanying colored photograph illustrates the overall appearance of the new Alstroemeria, showing the colors as true as it is reasonably possible to obtain in colored reproductions of this type. Colors in the photograph may differ slightly from the color values cited in the detailed botanical description which accurately describe the colors of the new Alstroemeria. The photograph comprises a side perspective view of typical flowers of 'Stamaria'.

DETAILED BOTANICAL DESCRIPTION

The aforementioned photograph, following observations and measurements describe plants of the new Alstroemeria grown in Rijsenhout, The Netherlands in a glass-covered greenhouse in ground beds. During the production of the plants, day temperatures ranged from 15 to 25° C. and night temperatures ranged from 10 to 15° C. Plants used for the photograph and description were about 12 months from planting root divisions. The photograph and the description were taken during August and September, 2001.

Color references are made to The Royal Horticultural Society Colour Chart, 1995 Edition, except where general terms of ordinary dictionary significance are used.

Botanical classification: *Alstroemeria hybrida* cultivar Stamaria.

Parentage:

*Female parent.*—Proprietary *Alstroemeria hybrida* selection identified as 89T935-1, not patented.

*Male parent.*—Proprietary selection of *Alstroemeria hybrida* identified as 86G713-1, not patented.

Propagation:

*Type.*—By root divisions.

*Root description.*—Fibrous, fleshy; white, close to 155D, in color.

*Rooting habit.*—Freely branching.

*Rhizomes.*—Shape: Elongate; rounded. Length: About 10 to 30 cm. Diameter: About 0.3 to 1 cm. Texture: Smooth. Color: Close to 155D.

Plant description:

*Plant habit.*—Upright; freely basal branching, bushy appearance.

*Time from planting to harvest of cut flowers.*—About 80 to 90 days.

*Number of flowering stems produced per year.*—About 220 to 240.

*Plant height.*—About 125 to 175 cm.

*Plant diameter* (*spread*).—About 25 to 30 cm.

*Flowering stem description.*—Aspect: Erect. Length: About 160 cm. Diameter: About 7 to 10 mm. Internode length: About 4 to 6 cm. Strength: Strong. Texture: Glabrous. Color: Close to 144A to 144B.

*Foliage description.*—Leaves asymmetrical; sessile. Length: About 17 to 20 cm. Width: About 3.5 to 4 cm. Shape: Lanceolate to linear. Apex: Acute. Base: Attenuate. Margin: Entire. Texture, upper and lower surfaces: Glabrous. Venation pattern: Parallel. Color: Young and fully developed foliage, upper surface: Close to 137A; glossy. Young and fully developed foliage, lower surface: Close to 137C. Venation: Upper surface, close to 137A; lower surface, close to 137C.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 20 to 25 days.

*Flower buds* (*showing color*).—Length: About 4 to 5 cm. Diameter: About 1.5 cm. Shape: Roughly ovoid. Color: Close to 52A.

*Umbel length.*—About 17 to 20 cm.

*Umbel diameter.*—About 20 to 30 cm.

*Number of flowers per umbel.*—About 20 to 25.

*Flower length.*—About 5 to 6 cm.

*Flower diameter.*—About 5.5 to 6.5 cm.

*Flower depth.*—About 5 to 5.5 cm.

*Perianth.*—Arrangement: Six arranged in two whorls, each whorl with two lateral and one median segments. Size: Inner perianth: Length: Laterals, about 5.5 to 5.7 cm; median, 4.2 to 4.5 cm. Width: Laterals, about 1.5 to 1.6 cm; median, about 1.5 to 1.8 cm. Outer perianth: Length: Laterals, about 5.1 to 5.3 cm; median, about 5.3 to 5.5 cm. Width: Laterals, about 3.2 to 3.5 cm; median, about 3.3 to 3.7 cm. Shape: Inner perianth, all segments: Oblanceolate. Outer perianth, all segments: Obovate. Apex: Inner perianth, all segments: Acute. Outer perianth, all segments: Emarginate. Base, inner and outer perianths, all segments: Attenuate. Margin, inner and outer perianths, all segments: Entire. Texture, inner and outer perianths, all segments: Smooth, glabrous; velvety. Color: Inner perianth: When opening and fully opened, upper surface: Laterals: Towards apex, close to 41B; towards base, close to 9A; spots and stripes, close to 187A. Median: Towards apex, close to 39A; towards margins, close to 20B; towards base, close to 52A; spots and stripes, close to 187A. When opening and fully opened, lower surface: Laterals: Towards apex, close to 41C; towards base, close to 9A. Median: Towards apex, close to 41D; towards base, close to 20B. Outer perianth: When opening and fully opened, upper surface, laterals and median: Center, close to 52A; towards margins, close to 19A to 20A; at emargination, close to 53A. When opening and fully opened, lower surface, laterals and median: Towards apex, close to 52B; towards base, close to 29D.

*Pedicels.*—Length: About 1.5 to 2 cm. Diameter: About 2 to 4 mm. Strength: Strong. Angle: About 30 to 60° from vertical. Texture: Smooth, glabrous. Color: Close to 144A.

*Reproductive organs.*—Stamens: Quantity per flower: Six. Anther shape: Elliptical. Anther length: About 8 mm. Anther diameter: About 3 mm. Anther color: Close to 164A. Pollen amount: Scarce. Pollen color: Close to 151A. Pistils: Quantity per flower: One. Style length: About 4 to 4.5 cm. Stigma color: Orange. Ovary color: Close to 144B.

*Fruit.*—Shape: Globular. Color: Brown.

Disease/pest resistance: Plants of the new Alstroemeria have not been observed to be resistant to pathogens and pests common to Alstroemerias.

Temperature tolerance: Plants of the new Alstroemeria have been observed to tolerate temperatures from −5 to 40° C.

It is claimed:

1. A new and distinct cultivar of Alstroemeria plant named 'Stamaria', as illustrated and described.

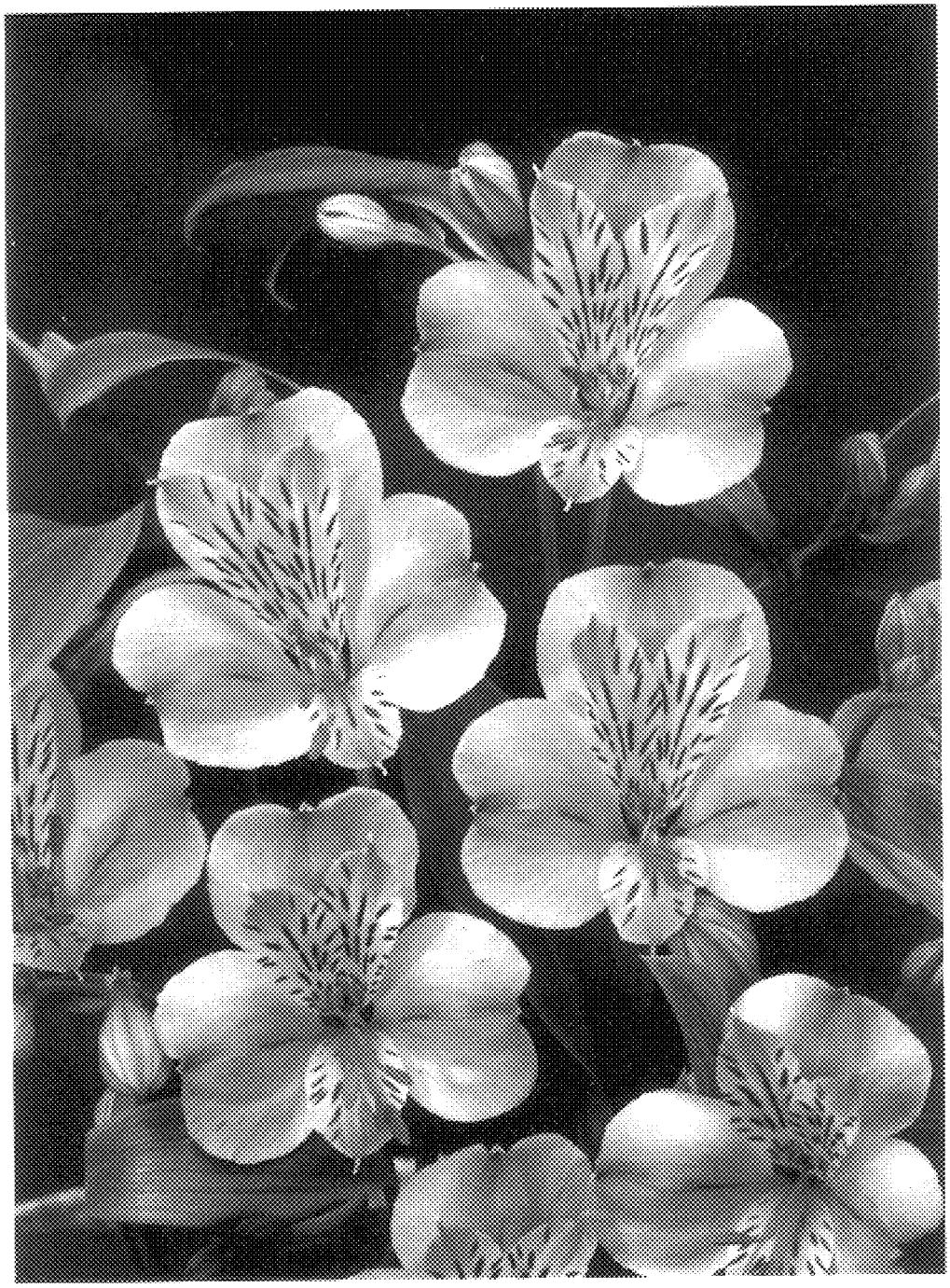

* * * * *